(12) United States Patent
Martin, Sr.

(10) Patent No.: US 10,188,558 B1
(45) Date of Patent: Jan. 29, 2019

(54) MALE URINARY INCONTINENCE DEVICE

(71) Applicant: Larry Sinatra Martin, Sr., Old Hickory, TN (US)

(72) Inventor: Larry Sinatra Martin, Sr., Old Hickory, TN (US)

( * ) Notice: Subject to any disclaimer, the term of this patent is extended or adjusted under 35 U.S.C. 154(b) by 0 days.

(21) Appl. No.: 15/863,234

(22) Filed: Jan. 5, 2018

(51) Int. Cl.
| | |
|---|---|
| A61F 13/47 | (2006.01) |
| A61F 13/56 | (2006.01) |
| A61F 13/471 | (2006.01) |
| A61F 13/474 | (2006.01) |

(52) U.S. Cl.
CPC ........ *A61F 13/471* (2013.01); *A61F 13/4704* (2013.01); *A61F 13/474* (2013.01); *A61F 13/5611* (2013.01)

(58) Field of Classification Search
CPC .. A61F 13/471; A61F 13/4704; A61F 13/474; A61F 13/5611
USPC .......................................... 604/353
See application file for complete search history.

(56) References Cited

U.S. PATENT DOCUMENTS

| | | | |
|---|---|---|---|
| 4,576,599 A * | 3/1986 | Lipner ................ | A61F 5/4401 604/352 |
| 4,601,716 A | 7/1986 | Smith | |
| 4,675,012 A * | 6/1987 | Rooyakkers ......... | A61F 5/4401 604/349 |
| 4,790,835 A | 12/1988 | Elias | |
| 4,971,074 A | 11/1990 | Hrubetz | |
| 6,209,142 B1 * | 4/2001 | Mattsson ............. | A61F 5/453 2/400 |
| 6,336,919 B1 * | 1/2002 | Davis .................. | A61F 5/453 604/346 |
| 6,479,726 B1 | 11/2002 | Cole | |
| 6,540,729 B1 * | 4/2003 | Wada .................. | A61F 13/471 604/349 |
| 6,569,135 B1 * | 5/2003 | Mula .................. | A61F 13/471 604/347 |
| 6,949,090 B1 | 9/2005 | Leers et al. | |
| D613,855 S | 4/2010 | Pena | |
| 8,250,677 B2 | 8/2012 | Nicolosi et al. | |
| 8,298,202 B2 | 10/2012 | McCray | |
| 2003/0023222 A1 | 1/2003 | Chen | |
| 2014/0358098 A1 | 12/2014 | Henderson | |

* cited by examiner

*Primary Examiner* — Tarla R Patel
(74) *Attorney, Agent, or Firm* — Shane Cortesi

(57) ABSTRACT

A male urinary incontinence device in the form of a penis wrap is disclosed. The wrap may include a distal region and a proximal region, which may be in the form of multi-layered absorbent pads. The distal region may be foldable toward the proximal region so that the head of the penis is located between the distal and proximal regions. The regions may be subsequently folded twice widthwise and secured with fasteners.

24 Claims, 6 Drawing Sheets

MALE URINARY INCONTINENCE DEVICE

BACKGROUND

Technical Field

The present invention relates to urinary incontinence devices for males.

Background of the Invention

Urinary incontinence, in which the ordinary bodily muscle functions fail to prevent unintended leakage of urine, is a common issue among men, particularly older men.

Examples of prior urinary incontinence devices include a diaper disclosed in U.S. Pat. No. 4,790,085. However, it is believed that the diaper would be uncomfortable. Another example is a sheath disclosed in U.S. Pat. No. 4,601,716. However, the sheath appears bulky, which can be problematic because the user desires that the product be worn discretely.

Thus, there is a need for new male urinary incontinence devices that are both effective and comfortable.

BRIEF SUMMARY

The present disclosure provides a male urinary incontinence device as described herein.

In some embodiments, the present disclosure provides a method of treating urinary incontinence in a male having a penis having a penis head, the method comprising the steps of: a) providing a wrap configured to absorb urine, the wrap comprising a front surface, a rear surface opposite the front surface, a left side, a right side, a length extending from the left side to the right side, a lengthwise center located in the center of the length, a proximal end, a distal end, a width extending from the proximal end to the distal end and generally perpendicular to the length; b) placing the head of the penis of the male on a portion of the front surface; c) before or after step b), folding the distal end toward the proximal end along a lengthwise foldline generally parallel to the length so that a portion of the front surface (i.e., a portion adjacent the distal end) is located in front of and faces another portion (i.e., a portion adjacent to the proximal end) of the front surface; and d) after step c), folding the left side of the folded wrap toward the head of the penis along a left widthwise foldline generally parallel to the width and folding the right side toward the head of the penis along a right widthwise foldline generally parallel to the width to secure the head of the penis in the wrap. Optionally, after steps b) and c), the head of the penis is located between the portions of the front surface. Optionally, during step d) at least one of the left side and the right side comprise a fastener and the method further comprises, during step d), attaching the fastener to the wrap rear surface. Optionally, the fastener is configured to removably attach to the rear surface. Optionally, the left side and right side each comprise a fastener, and step d) comprises, after step c), folding the left side of the folded wrap toward the lengthwise center and the head of the penis along the left widthwise foldline and attaching the left side fastener to the rear surface (and toward the right widthwise foldline) and then folding the right side toward the lengthwise center and toward the head of the penis (and toward the left widthwise foldline) along the right widthwise foldline and attaching the right side fastener to the rear surface to secure the head of the penis in the wrap. Optionally, the left side and right side each comprise a fastener, and step d) comprises, after step c), folding the right side of the folded wrap toward the lengthwise center and toward the head of the penis (and toward the left widthwise foldline) along the right widthwise foldline and attaching the right side fastener to the rear surface and then folding the left side toward the lengthwise center and toward the head of the penis (and toward the right widthwise foldline) along the left widthwise foldline and attaching the left side fastener to the rear surface to secure the head of the penis in the wrap. Optionally, in step a), the wrap further comprises a front pad located in front of the wrap and step b) comprises placing the head of the penis on the front pad. Optionally, the wrap is stretchable. Optionally, in step a), the wrap is comprised of a plurality of layers. Optionally, in step a), the wrap is generally rectangular in shape and has rounded corners. Optionally, in step a), the rear surface comprises at least one fastener. Optionally, in step c), the wrap is generally in the shape of an envelope.

In still further embodiments, the present disclosure provides a method of treating urinary incontinence in a male having a penis having a penis head, the method comprising the steps of: a) providing a wrap configured to absorb urine and having: i) a distal region comprising one or more materials configured to absorb urine, the distal region further comprising a front surface, a rear surface opposite the front surface, a distal region left side, a distal region right side, a distal region length extending from the distal region left side to the distal region right side, a distal region proximal end, a distal region distal end, a distal region width extending from the distal region proximal end to the distal region distal end and generally perpendicular to the distal region length; ii) a lengthwise foldline located at the proximal end of the distal region and extending generally parallel to the distal region length; iii) a proximal region comprising one or more materials configured to absorb urine, the proximal region further comprising a proximal region distal end attached to the distal region at the lengthwise foldline, the proximal region further comprising a proximal region proximal end, a proximal region width extending from the proximal region proximal end to the proximal region distal end, a proximal region left side, a proximal region right side, a length extending from the proximal region left side to the proximal region right side; iv) a left widthwise foldline extending through the proximal and distal regions generally along the proximal and distal region widths; and v) a right widthwise foldline located to the right of the left widthwise foldline and extending through the proximal and distal regions generally along the proximal and distal region widths. Optionally, the method further comprises: b) placing the head of the penis of the male on the proximal region front surface; c) before or after step b), folding the distal region along the lengthwise foldline so that the distal region front surface faces the proximal region front surface; and d) folding the left side of the proximal region and the left side of the distal region together along the left widthwise foldline toward the head of the penis and folding the right side of the proximal region and the right side of the distal region together along the right widthwise foldline toward the head of the penis to secure the head of the penis in the wrap. Optionally, after steps b) and c), the head of the penis is located between the front surface of the proximal region and the front surface of the distal region. Optionally, at least one of the proximal region front surface left side and the proximal region front surface right side comprise a fastener configured to removably attach to the distal region rear surface and the method further comprises, during step d), attaching the fastener to the distal region rear surface. Optionally, each of the proximal region left side and the proximal region right side comprise a fastener configured to removably attach to the distal region rear surface and the method further comprises, during step d), attaching the fasteners to the distal region rear surface. Optionally, in step a) (and step c), the fastener of the proximal region left side is located to the left of the left side of the distal region and the fastener of the proximal region right side is located to the right of the right side of the distal region. Optionally, the front surface of the proximal region left side comprises a left side fastener configured to removably attach to the distal region rear surface, wherein the front surface of the proximal region right side comprises a right side fastener configured to removably attach to the distal region rear surface, wherein step d) comprises folding the left side of the proximal region and the left side of the distal region together along the left widthwise foldline toward the head of the user's penis (and toward the right widthwise foldline), attaching the left side fastener to the distal region rear surface, and then folding the right side of the proximal region and the right side of the distal region together along the right widthwise foldline toward the head of the penis (and toward the left widthwise foldline), and attaching the right side fastener to the distal region rear surface, and further wherein after step d), the left sides of the proximal region and distal region are located behind the right sides of the proximal region and the distal region. Optionally, the front surface of the proximal region left side comprises a left side fastener configured to removably attach to the distal region rear surface, wherein the front surface of the proximal region right side comprises a right side fastener configured to removably attach to the distal region rear surface, wherein step d) comprises folding the right side of the proximal region and the right side of the distal region together along the right widthwise foldline toward the head of the user's penis (and toward the left widthwise foldline), attaching the right side fastener to the distal region rear surface, and then folding the left side of the proximal region and the left side of the distal region together along the left widthwise foldline toward the head of the penis (and toward the right widthwise foldline), and attaching the left side fastener to the distal region rear surface, and further wherein after step d), the left sides of the proximal region and distal region are located in front of the right sides of the proximal region and the distal region. Optionally, in step b), the head of the penis of the male is placed below the lengthwise foldline and does not contact the distal region. Optionally, in step a), the distal region length is less than the proximal region length. Optionally, in step a), the distal region width and the proximal region width are substantially equal. Optionally, in step a), a portion of the proximal region front surface, a portion of the lengthwise foldline, and a portion of the distal region front surface comprise a front pad and step b) comprises placing the head of the penis on the front pad. Optionally, the distal region and the proximal region are stretchable. Optionally, the distal region and the proximal region are each comprised of a plurality of layers. Optionally, in step a), the distal region and proximal region are generally rectangular in shape and have rounded corners. Optionally, the distal region rear surface comprises at least one fastener. Optionally, after step c), the wrap is generally in the shape of an envelope. Optionally, in step a), the lengthwise foldline is the sole attachment of the distal region to the proximal region. Optionally, the method further comprises the step of absorbing urine onto the wrap. Optionally, in step d), the left and right widthwise foldlines divides the distal region into three units of approximately equal length and approximately equal width.

BRIEF DESCRIPTION OF THE DRAWINGS

in FIG. 1, the wrap is not folded.

in FIG. 2 the wrap is not folded.

in FIG. 3, the wrap is not folded.

in FIG. 4 the wrap is not folded and a penis has been laid onto the wrap front surface.

in FIG. 5, the wrap has been folded along the lengthwise foldline.

in FIG. 6, the wrap has been folded along the right widthwise foldline.

in FIG. 7, the wrap has been folded along the left widthwise foldline.

in FIG. 1, the wrap is not folded.

in FIG. 9 the wrap is not folded.

in FIG. 10 the wrap is not folded and a penis has been laid onto the wrap front surface.

in FIG. 10, the wrap has been folded along the lengthwise foldline.

in FIG. 12, the wrap has been folded along the left widthwise foldline.

in FIG. 13, the wrap has been folded along the right widthwise foldline.

DETAILED DESCRIPTION

Figure 1:
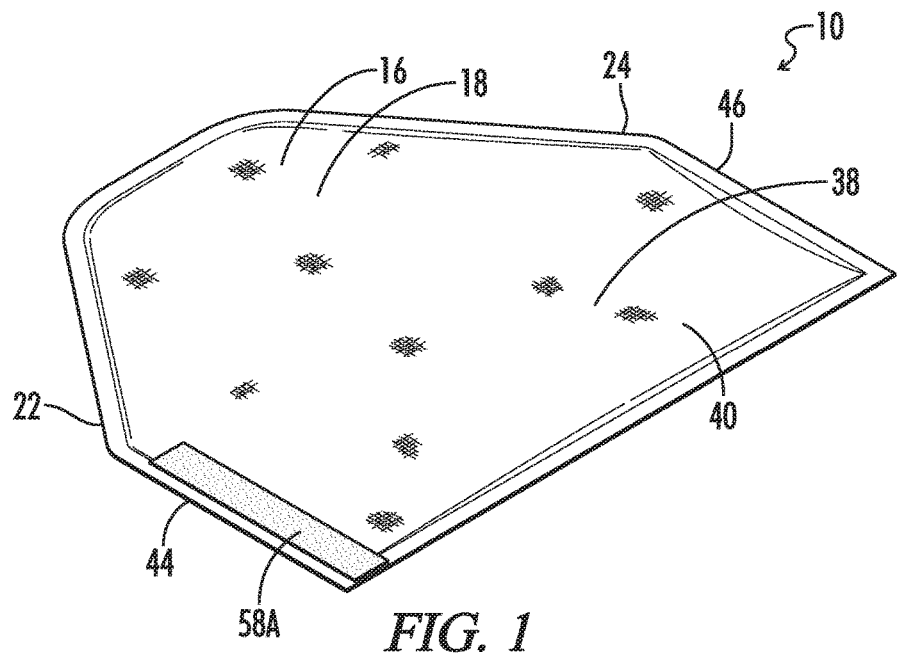
FIG. 1 is a front perspective view of a wrap of one embodiment of the present invention.
Figure 2:
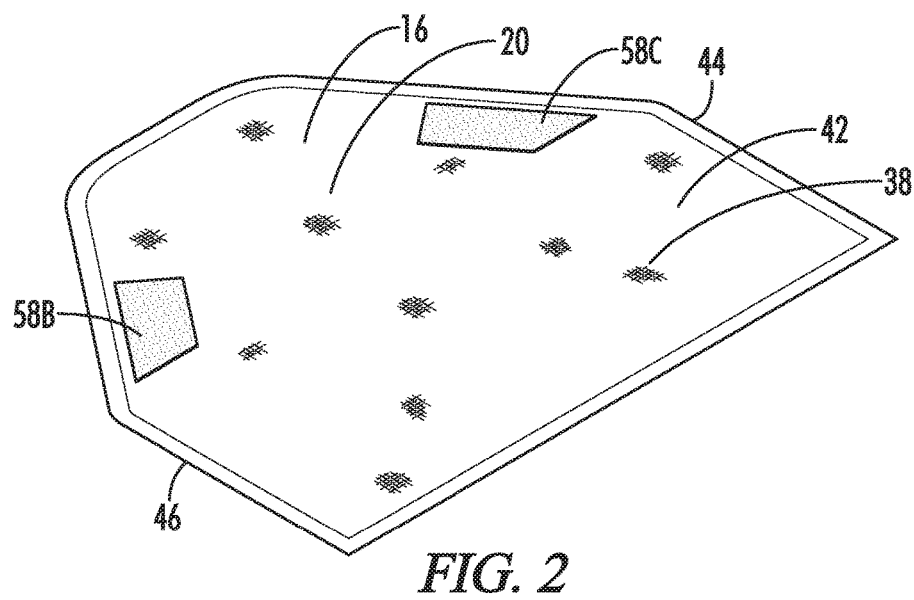
FIG. 2 is a rear perspective view of the wrap of FIG. 1.
Figure 3:
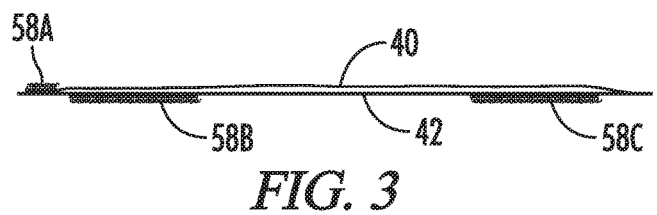
FIG. 3 is a distal elevation view of the wrap of FIG. 1.
Figure 4:
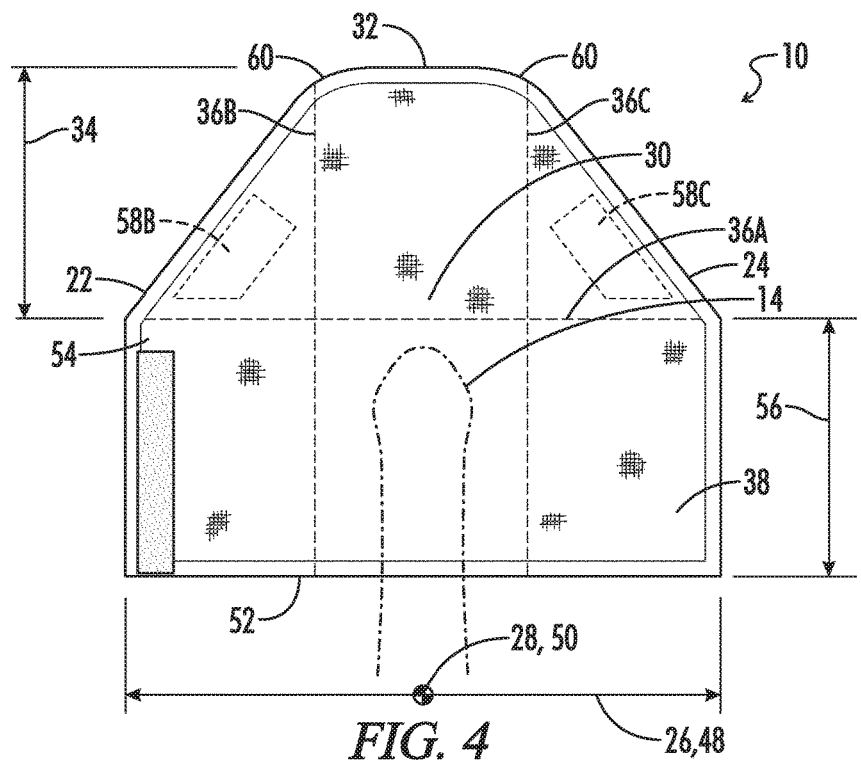
FIG. 4 is a front perspective view of the wrap of FIG. 1.

With reference to FIGS. 1-13, the present invention provides a wrap configured to treat male urinary incontinence generally designated by the numeral 10. In the drawings, not all reference numbers are included in each drawing for the sake of clarity.

Referring further to FIGS. 1-13, the wrap 10 may be comprised of one or more absorbent layers configured to absorb urine. In some embodiments, the wrap 10 is comprised of absorbent layers typically found in diapers, including without limitation the PAMPERS or HUGGIES line of diapers. In some embodiments, the wrap 10 interior includes beads that are configured to absorb urine. Optionally, the wrap includes a cover. Diapers and diaper material are well-known in the art and are described in for example U.S. Pat. Nos. 9,216,118, 7,744,576, 7,750,203, 7,851,66, 8,187, 240, 8,674,170, 8,766,031, 8,927,801, 8,979,815, 9,173,784, 9,2116,116, 9,480,611, 9,265,674, 9,265,473, 9,138,362 and 6,406,467, the entire contents of all of which are incorporated herein by reference.

Referring further to FIGS. 1-13, two different embodiments of a wrap 10 are shown in the illustrations, with a first embodiment shown in FIGS. 1-7 and a second embodiment shown in FIGS. 8-13. The wrap 10 may include a front surface 18 and 40, a rear surface 20 and 42 opposite the front surface 18 and 40, a left side 22 and 44, a right side 24 and 46, a length 26 and 48 extending from the left side 22 and 44 to the right side 24 and 46, a lengthwise center 28 and 50 located in the center of the length 26 and 48, a proximal end 52 (more particularly a proximal region proximal end 52), a distal end 32 (more particularly a distal region distal end 32), a width extending from the proximal end to the distal end and generally perpendicular to the length 26 and 48. (Many of these components have two numerals because the wrap may include a proximal region 38 and a distal region 16 as explained below). A user may place the head of his penis on a portion of the front surface 40. See FIGS. 4 and 10. Before or after placing the head 14 of his penis 12 on the front surface 40, the user may fold the distal region distal end 32 relative to the head 14 of the penis 12 (toward the proximal region proximal end 52) along a lengthwise foldline 36A and 36D generally parallel to the length 26 and 48 so that a portion of the front surface 18 (more particularly distal region front surface 18) is now located in front of and faces another portion of the front surface 40 (more particularly proximal region front surface 40). See FIGS. 5 and 11. It will be understood that the terms "front surface", "rear surface", "proximal", "distal", "left side" and "right side" refer to the unfolded configuration shown in FIGS. 1, 4, 8 and 10. After the head 14 of the penis 12 is located between the portions of the front surface 18 and 40, the user then moves/folds the left side 22 and 44 of the folded wrap toward the lengthwise center 28 and 50 and the head 14 of the penis 12 along a left widthwise foldline 36B and 36E generally parallel to the width (see FIGS. 7 and 12) and also moves/folds the right side 24 and 46 toward the lengthwise center 28 and 50 and the head 14 of the penis 12 along a right widthwise foldline 36C and 36F generally parallel to the width to secure the head 14 of the penis 12 in the wrap 10 (see FIGS. 6 and 13). Either the left side 22 and 44 or right side 24 and 46 may be folded first.

More particularly, the wrap 10 may include i) a distal absorbent region 16 (shown as the top region in FIGS. 1-2, 4 and 8-10) comprising one or more materials configured to absorb urine, the distal region 16 further comprising a front surface 18, a rear surface 20 opposite the front surface 18, a distal region left side 22, a distal region right side 24, a distal region length 26 extending from the distal region left side 22 to the distal region right side 24, a distal region lengthwise center 28 located in the center of the distal region length 26, a distal region proximal end 30, a distal region distal end 32, a distal region width 34 extending from the distal region proximal end 30 to the distal region distal end 32 and generally perpendicular to the distal region length 26; ii) a lengthwise foldline 36A and 36D located at the proximal end 30 of the distal region 16 and extending generally parallel to the distal region length 26; iii) a proximal absorbent region 38 (shown as the bottom region in FIGS. 1-2, 4 and 8-10) comprising one or more materials configured to absorb urine, the proximal region 38 further comprising a proximal region distal end 54 attached to the distal absorbent region 16 at the lengthwise foldline 36A and 36D, the proximal region 38 further comprising a proximal region proximal end 52, a proximal region width 56 extending from the proximal region proximal end 52 to the proximal region distal end 54, a proximal region left side 44, a proximal region right side 46, a length 48 extending from the proximal region left side 44 to the proximal region right side 46, and a proximal region lengthwise center 50 located in the center of the proximal region length 48; iv) a left widthwise foldline 36B and 36E extending through the proximal and distal regions 16 and 38 generally along the widths 34 and 56; and v) a right widthwise foldline 36C and 36F located to the right of the left widthwise foldline 36B and 36E and extending through the proximal and distal regions 16 and 38 generally along the widths 34 and 56. The distal and proximal regions 16 and 38 may or may not be discrete panels. Likewise, the foldlines 36A-F herein may or may not be defined lines. More particularly, in some embodiments, the distal region 16 and proximal region 38 are separate panels that are joined together at a lengthwise foldline 36A and 36D pre-defined by the manufacturer. In other embodiments, the distal and proximal regions 16 and 38 are part of a single panel and the lengthwise foldline 36A and 36D may be defined by the user during the folding process. Likewise, the widthwise foldlines 36B, 36C, 36E and 36F may be pre-defined the manufacturer or by the user. If the foldlines 36A-E are defined by the user during the folding process, the wrap 10 may or may not have visible lines to assist the user.

The user may place the head 14 of his penis 12 on the proximal region front surface 40. See FIGS. 4 and 10. Before or after placing the head 14 of his penis 12 on the proximal region front surface 40, the user may fold the distal region 16 along the lengthwise foldline 36A and 36D so that the distal region front surface 18 faces the proximal region front surface 40. See FIGS. 5 and 11. After the head 14 of the user's penis 12 is located between the distal region front surface 18 and proximal region front surface 40, the user may then fold the left side of the proximal region 44 and the left side of the distal region 22 together along the left widthwise foldline 36B and 36E toward the distal region lengthwise center 28 (see FIGS. 7 and 12) and the proximal region lengthwise center 50 and fold the right side 46 of the proximal region 38 and the right side 24 of the distal region 16 together along the right widthwise foldline 36B and 36F toward the distal region lengthwise center 28 and the proximal region lengthwise center 50 to secure the head 14 of the penis 12 in the wrap 10 (see FIGS. 6 and 13). Again, it will be understood that the terms "front surface", "rear surface", "proximal", "distal", "left side" and "right side" refer to the unfolded configuration shown in FIGS. 1, 4, 8 and 10.

Figure 8:
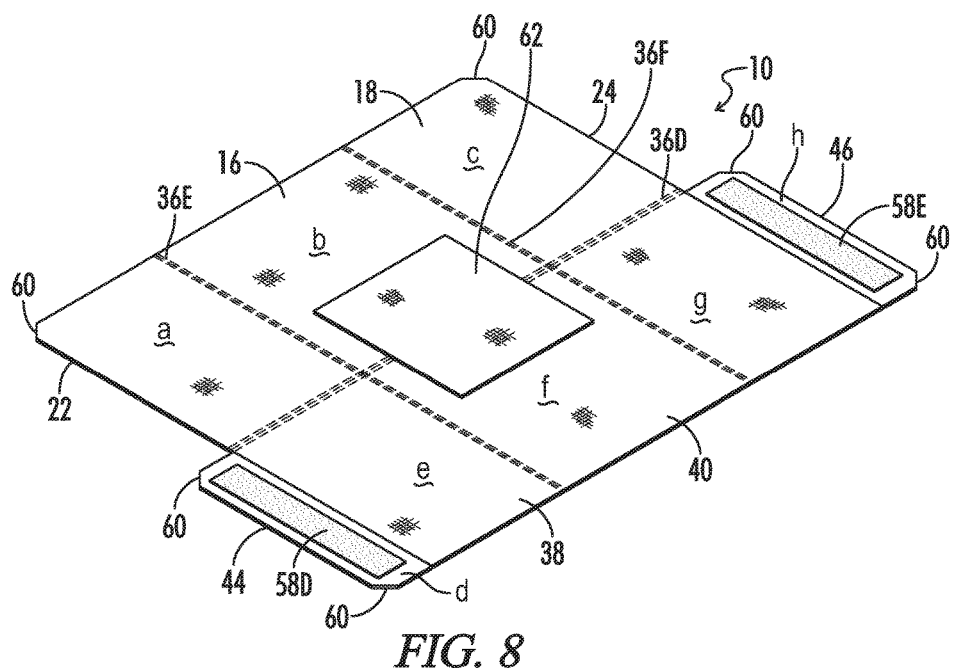
FIG. 8 is a front perspective view of a wrap of another embodiment of the present invention.
Figure 9:
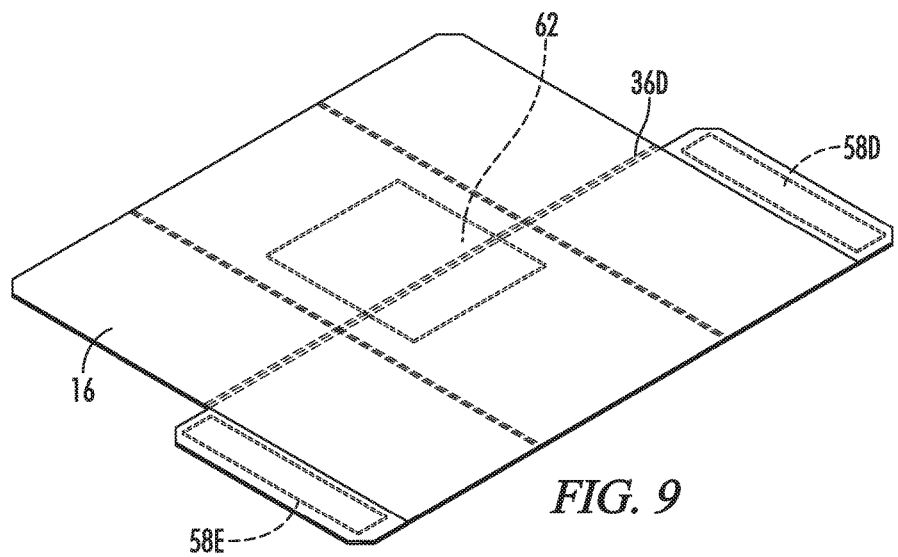
FIG. 9 is a rear perspective view of the wrap of FIG. 8.
Figure 10:
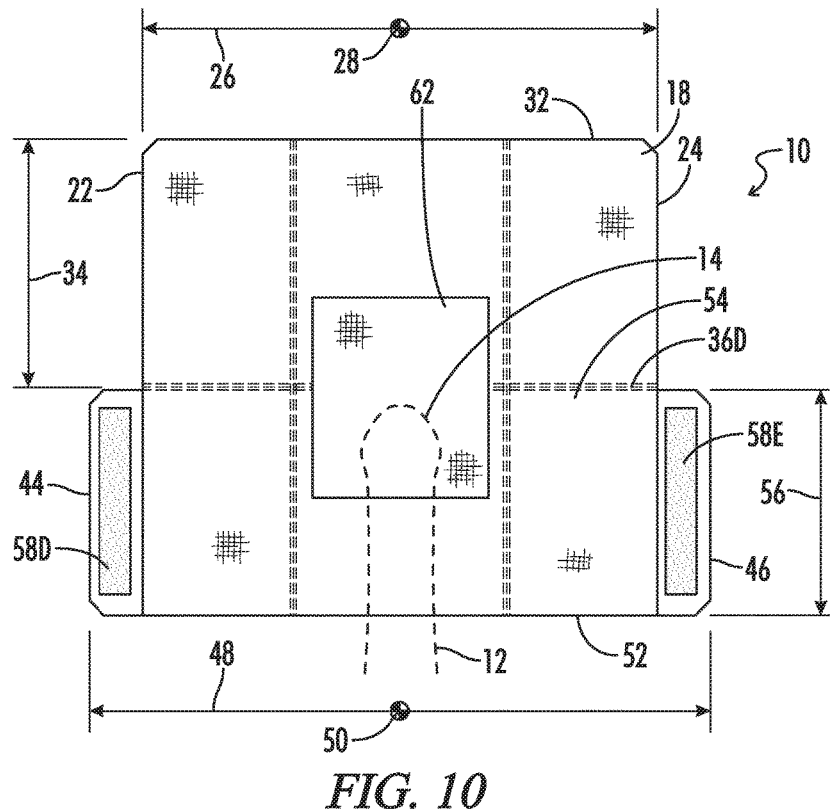
FIG. 10 is a front perspective view of the wrap of FIG. 8.
Figure 11:
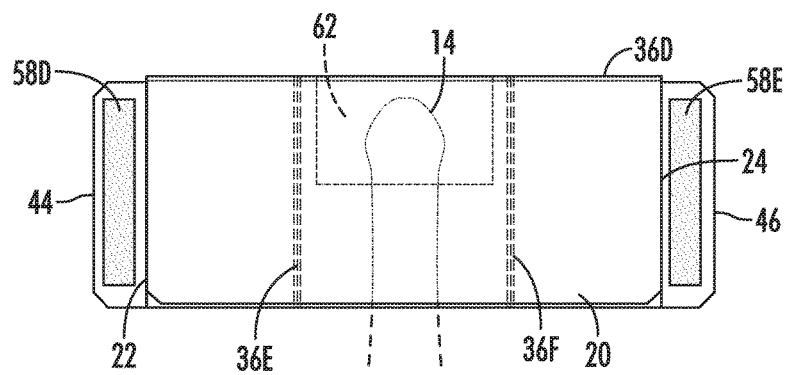
FIG. 11 is a front perspective view of the wrap and penis of FIG. 8.
Figure 12:
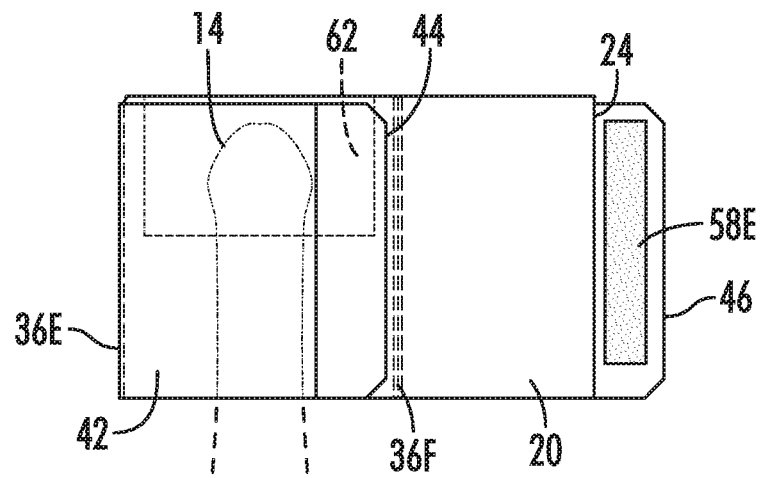
FIG. 12 is a front perspective view of the wrap and penis of FIG. 8.
Figure 13:
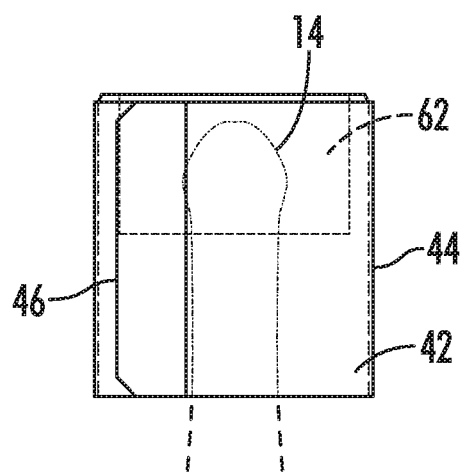
FIG. 13 is a front perspective view of the wrap and penis of FIG. 1.

Optionally, at least one of the proximal region front surface left side 44 and the proximal region front surface right side 46 comprise a fastener 58A, 58D and 58E configured to removably attach to the distal region rear surface 20 and the method further comprises attaching the fastener 58A, 58D and 58E to the distal region rear surface 20. See FIGS. 5 and 12. It will be understood that the fasteners 58A, 58D and 58E may be slightly indented from the left side 44 and right side 46, as best seen in FIG. 11. Fasteners 58A-E used herein may be hook and loop or for example, removable adhesives that are found on diapers. Optionally, the front surface 40 of the proximal region left side 44 comprises a fastener 58A and 58D configured to removably attach to the distal region rear surface 20, wherein the method further comprises attaching the fastener 58A and 58D to the distal region rear surface 20. Optionally, if the right sides 24 and 46 are folded first, after folding along both the left and right widthwise foldlines 36B, 36C, 36E and 36F, the left sides 22 and 44 of the proximal region 38 and distal region 16 are located in front of the right sides 24 and 46 of the proximal region 38 and the distal region 16 (see FIG. 7 for example). Alternatively, if the right sides 24 and 46 are folded last, after folding along both the left and right widthwise foldlines 36B, 36C, 36E and 36F, the left sides 22 and 44 of the proximal region 38 and distal region 16 may be located behind the right sides 24 and 46 of the proximal region 38 and the distal region 16 (see FIG. 13 for example). The fasteners 36D-36E may be located on two tabs that form the left side 44 and right side 46 of the proximal region 38, for example as shown in FIGS. 9-11 and the tabs may not themselves be comprised of absorbent material. As used herein, the tabs will be considered the left side 44 and right side 46 of the proximal region 38. As shown in FIG. 8, the distal region 16 may be divided into three generally rectangular subregions, a, b, and c, and the proximal region 38 may be divided into five generally rectangular subregions, d, e, f, g and h. (a and b are separate by foldline 36E, b and c are separated by foldline 36F, a and e are separated by foldline 36D, b and f are separated by foldline 36D, c and g are separated by foldline 36D, d is left tab and h is right tab). Subregions a-h each may have a width of about 3 inches, subregions a, c, e, and g may have a length of about 1.75 inches, subregions b and f may be slightly longer and have a length of about 2.25 inches and subregions d and h may be much narrower and have length of only about 0.5 inches. The length and width are given in the same orientation as the other components of the wrap 10—i.e., lengths 26 and 48 and widths 34 and 56. Such dimensions are exemplary and may vary by about 50 percent, more preferably 20 percent, more preferably 10 percent, and even more preferably less than 5 percent.

Figure 5:
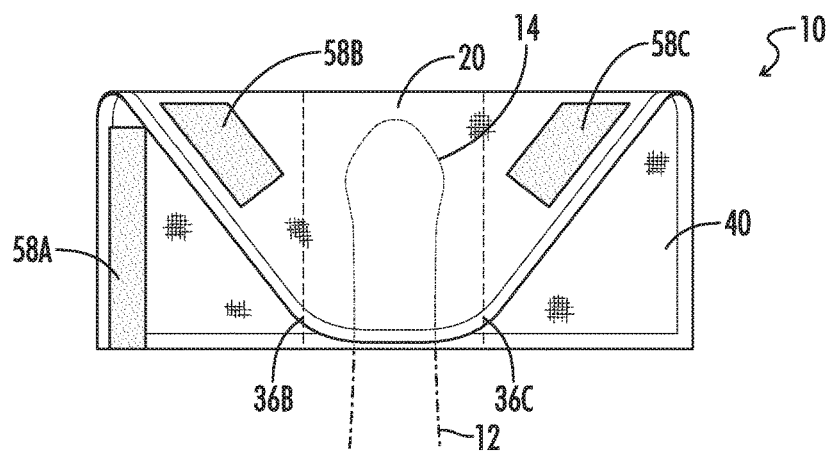
FIG. 5 is a front perspective view of the wrap and penis of FIG. 1.
Figure 6:
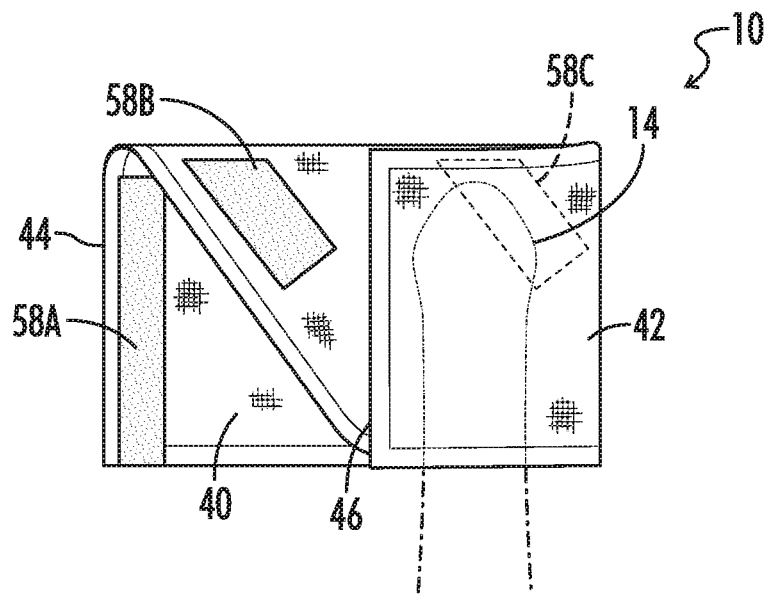
FIG. 6 is a front perspective view of the wrap and penis of FIG. 1.
Figure 7:
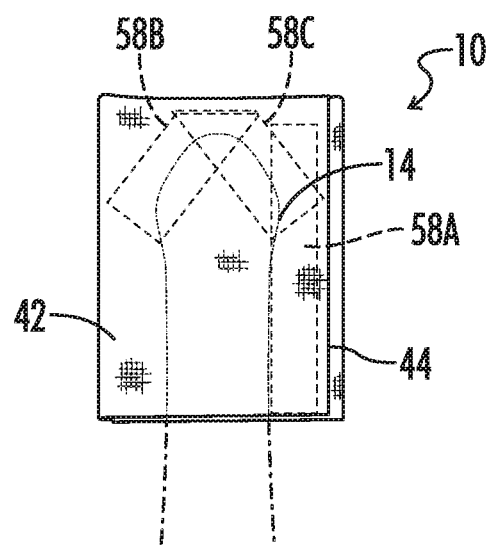
FIG. 7 is a front perspective view of the wrap and penis of FIG. 1.

Optionally, in step a), the fastener 36D of the proximal region left side 44 is located to the left of the left side 22 of the distal region 16 and the fastener 36E of the proximal region right side 46 is located to the right of the right side 24 of the distal region 16, as shown in FIGS. 8 and 10 for example. Optionally, the front surface 40 of the proximal region right side 46 comprises a fastener 58E configured to removably attach to the distal region rear surface 20, and the method further comprises attaching the fastener 58E to the distal region rear surface 20. Optionally, the head 14 of the penis 12 of the male is placed below the lengthwise foldline 36A and 36D and does not contact the distal region 16. See FIGS. 4 and 10. Optionally, the distal region length 26 is less than the proximal region length 48, as shown in FIGS. 8-13. Optionally, the distal region width 34 and the proximal region width 56 are substantially equal, as shown in FIGS. 1-13. Optionally, as shown in FIGS. 8-13, a portion of the proximal region front surface 40, a portion of the lengthwise foldline 36A and 36D, and a portion of the distal region front surface 18 and 40 comprises a front pad 62 and the method comprises placing the head 14 of the penis 12 on the front pad 62. Optionally, the distal region 16 and the proximal region 38 are stretchable, e.g., at least partially elastic like diapers. Optionally, the distal region 16 and proximal region 38 are generally rectangular in shape and have rounded corners 60, as shown in FIGS. 8-13. Optionally, as shown in FIGS. 1-7, the distal region rear surface 20 comprises at least one fastener 58B and 58C. Optionally, as shown in FIG. 5, after folding along the lengthwise foldine 36B, the wrap 10 is generally in the shape of an envelope. Optionally, the lengthwise foldline 36B and 36D is the sole attachment of the distal region 16 to the proximal region 38, as shown in FIGS. 1-13. Optionally, as shown in FIGS. 1-13, the left and right widthwise foldlines 36E and 36F separates the distal region 16 into three units of approximately equal length and approximately equal width.

Having now described the invention in accordance with the requirements of the patent statutes, those skilled in the art will understand how to make changes and modifications to the disclosed embodiments to meet their specific requirements or conditions. Changes and modifications may be made without departing from the scope and spirit of the invention. In addition, the steps of any method described herein may be performed in any suitable order and steps may be performed simultaneously if needed.

Terms of degree such as "generally", "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

What is claimed is:

1. A method of treating urinary incontinence in a human male having a penis having a penis head, the method comprising the steps of:
   a) providing a wrap configured to absorb urine and having:
      i) a distal region configured to absorb urine and comprised of a plurality of layers, the distal region further comprising a front surface, a rear surface opposite the front surface, a distal region left side, a distal region right side, a distal region length extending from the distal region left side to the distal region right side, a distal region proximal end, a distal region distal end, a distal region width extending from the distal region proximal end to the distal region distal end and generally perpendicular to the distal region length;
      ii) a lengthwise foldline located at the proximal end of the distal region and extending generally parallel to the distal region length;
      iii) a proximal region configured to absorb urine and comprised of a plurality of layers, the proximal region further comprising a proximal region distal end extending from the distal region at the lengthwise foldline, the proximal region further comprising a proximal region proximal end, a proximal region width extending from the proximal region proximal end to the proximal region distal end, a proximal region left side, a proximal region right side, a length extending from the proximal region left side to the proximal region right side;
      iv) a left widthwise foldline extending through the proximal and distal regions generally along the proximal and distal region widths; and
      v) a right widthwise foldline located to the right of the left widthwise foldline and extending through the proximal and distal regions generally along the proximal and distal region widths,
      wherein the front surface of the proximal region left side comprises a left side fastener configured to removably attach to the distal region rear surface, and wherein the front surface of the proximal region right side comprises a right side fastener configured to removably attach to the proximal region rear surface;
   b) placing the head of the penis of the male on the proximal region front surface;
   c) before or after step b), folding the distal region along the lengthwise foldline so that the distal region front surface faces the proximal region front surface; and
   d) folding the left side of the proximal region and the left side of the distal region together along the left widthwise foldline toward the head of the user's penis, attaching the left side fastener to the distal region rear surface, and then folding the right side of the proximal region and the right side of the distal region together along the right widthwise foldline toward the head of the penis, and attaching the right side fastener to the proximal region rear surface, wherein after step d), the right sides of the proximal region and distal region are located in front of the left sides of the proximal region and the distal region and further wherein after steps b) and c), the head of the penis is located between the front surface of the proximal region and the front surface of the distal region.

2. The method of claim 1 wherein, after step c), the fastener of the proximal region left side is exposed and located to the left of the left side of the distal region and the fastener of the proximal region right side is exposed and located to the right of the right side of the distal region, and further wherein, except for the fasteners of the proximal region left side and proximal region right side, the distal region substantially covers the proximal region.

3. The method of claim 1 wherein, in step a), the distal region length is less than the proximal region length and the distal region width and the proximal region width are substantially equal.

4. The method of claim 1 wherein, in step a), a portion of the proximal region front surface distal to the proximal region proximal end, a portion of the lengthwise foldline, and a portion of the distal region front surface proximal to the distal region distal end comprise a front pad and step b) comprises placing the head of the penis on the front pad below the lengthwise foldline.

5. The method of claim 1, wherein the distal region and the proximal region are each comprised of a plurality of layers configured to absorb urine.

6. The method of claim 1 wherein, in step a), the distal region and proximal region are generally rectangular in shape and have rounded corners.

7. The method of claim 1 wherein, in step a), the lengthwise foldline is the sole attachment of the distal region to the proximal region.

8. The method of claim 1 further comprising the step of ejecting urine from the penis and absorbing urine onto the wrap.

9. The method of claim 1 wherein after steps a) through d), the wrap captures only a portion of the penis.

10. The method of claim 1 wherein after steps a) through d), the wrap is generally flat.

11. The method of claim 1 wherein the proximal region left side and right side fasteners are both rectangular strips that extend substantially the entire width of the proximal region.

12. The method of claim 1 wherein step d) comprises attaching the left side fastener directly to the distal region rear surface, and then folding the right side of the proximal region and the right side of the distal region together along the right widthwise foldline toward the head of the penis, and attaching the right side fastener directly to the proximal region rear surface.

13. A method of treating urinary incontinence in a human male having a penis having a penis head, the method comprising the steps of:
 a) providing a wrap configured to absorb urine and having:
  i) a distal region configured to absorb urine and comprised of a plurality of layers, the distal region further comprising a front surface, a rear surface opposite the front surface, a distal region left side, a distal region right side, a distal region length extending from the distal region left side to the distal region right side, a distal region proximal end, a distal region distal end, a distal region width extending from the distal region proximal end to the distal region distal end and generally perpendicular to the distal region length;
  ii) a lengthwise foldline located at the proximal end of the distal region and extending generally parallel to the distal region length;
  iii) a proximal configured to absorb urine and comprised of a plurality of layers, the proximal region further comprising a proximal region distal end extending from the distal region at the lengthwise foldline, the proximal region further comprising a proximal region proximal end, a proximal region width extending from the proximal region proximal end to the proximal region distal end, a proximal region left side, a proximal region right side, a length extending from the proximal region left side to the proximal region right side;
  iv) a left widthwise foldline extending through the proximal and distal regions generally along the proximal and distal region widths; and
  v) a right widthwise foldline located to the right of the left widthwise foldline and extending through the proximal and distal regions generally along the proximal and distal region widths,
  wherein the front surface of the proximal region left side comprises a left side fastener configured to removably attach to the distal region rear surface, and wherein the front surface of the proximal region right side comprises a right side fastener configured to removably attach to the proximal region rear surface;
 b) placing the head of the penis of the male on the proximal region front surface;
 c) before or after step b), folding the distal region along the lengthwise foldline so that the distal region front surface faces the proximal region front surface; and
 d) folding the right side of the proximal region and the right side of the distal region together along the right widthwise foldline toward the head of the user's penis, attaching the right side fastener to the distal region rear surface, and then folding the left side of the proximal region and the left side of the distal region together along the left widthwise foldline toward the head of the penis, and attaching the left side fastener to the proximal region rear surface, wherein after step d), the left sides of the proximal region and distal region are located in front of the right sides of the proximal region and the distal region, and further wherein after steps b) and c), the head of the penis is located between the front surface of the proximal region and the front surface of the distal region.

14. The method of claim 13 wherein, after step c), the fastener of the proximal region left side is exposed and located to the left of the left side of the distal region and the fastener of the proximal region right side is exposed and located to the right of the right side of the distal region.

15. The method of claim 13 wherein, in step a), the distal region length is less than the proximal region length and the distal region width and the proximal region width are substantially equal.

16. The method of claim 13 wherein, in step a), a portion of the proximal region front surface distal to the proximal region proximal end, a portion of the lengthwise foldline, and a portion of the distal region front surface proximal to the distal region distal end comprise a front pad and step b) comprises placing the head of the penis on the front pad below the lengthwise foldline.

17. The method of claim 13 wherein, in step a), the distal region and proximal region are generally rectangular in shape and have rounded corners.

18. The method of claim 13 wherein, in step a), the lengthwise foldline is the sole attachment of the distal region to the proximal region.

19. The method of claim 13 further comprising the step of ejecting urine from the penis and absorbing urine onto the wrap.

20. The method of claim 13 wherein after steps a) through d), the wrap captures only a portion of the penis.

21. The method of claim 13 wherein after steps a) through d), the wrap is generally flat.

22. The method of claim 13 wherein the proximal region left side and right side fasteners are both rectangular strips that extend substantially the entire width of the proximal region.

23. The method of claim 13, wherein the distal region and the proximal region are each comprised of a plurality of layers configured to absorb urine.

24. The method of claim 13, wherein step d) comprises folding the right side of the proximal region and the right side of the distal region together along the right widthwise foldline toward the head of the user's penis, attaching the right side fastener directly to the distal region rear surface, and then folding the left side of the proximal region and the left side of the distal region together along the left widthwise foldline toward the head of the penis, and attaching the left side fastener directly to the proximal region rear surface.

\* \* \* \* \*